(12) United States Patent
Maekawa et al.

(10) Patent No.: US 8,073,219 B2
(45) Date of Patent: Dec. 6, 2011

(54) NUCLEIC ACID ANALYZING APPARATUS

(75) Inventors: Akira Maekawa, Hitachinaka (JP);
Toshiro Saito, Hitachinaka (JP);
Kiyoyuki Kagii, Hitachinaka (JP);
Takayuki Obara, Tsuchiura (JP)

(73) Assignee: Hitachi High-Technologies Corporation, Tokyo (JP)

( * ) Notice: Subject to any disclaimer, the term of this patent is extended or adjusted under 35 U.S.C. 154(b) by 474 days.

(21) Appl. No.: 12/369,342

(22) Filed: Feb. 11, 2009

(65) Prior Publication Data

US 2009/0245604 A1 Oct. 1, 2009

(30) Foreign Application Priority Data

Mar. 31, 2008 (JP) ................................. 2008-093275

(51) Int. Cl.
*G06K 9/18* (2006.01)
(52) U.S. Cl. ....................................................... 382/128
(58) Field of Classification Search .................. None
See application file for complete search history.

(56) References Cited

U.S. PATENT DOCUMENTS 6,791,618 B1 9/2004 Shimizu

FOREIGN PATENT DOCUMENTS

| JP | 2000-180361 | 6/2000 |
|----|-------------|--------|
| JP | 2002-185724 | 6/2002 |
| JP | 2004-101376 | 4/2004 |
| JP | 2006-337245 | 12/2006 |
| JP | 2007-010325 | 1/2007 |
| JP | 2007-322185 | 12/2007 |

OTHER PUBLICATIONS

Braslavsky et al., "Sequence information can be obtained from single DNA molecules," Proceedings of the National Academy of Sciences of the United States of America, Apr. 1, 2003, vol. 100, No. 7, pp. 3960-3964.
Anger et al., "Enhancement and Quenching of Single-Molecule Fluorescence," The American Physical Society, 2006, vol. 96, No. 11, pp. 113002-1-113002-4.
Fu et al., "Enhanced Fluorescence and Cy5-Labeled DNA Tethered to Silver Island Films: Fluorescence Images and Time-Resolved Studies Using Single-Molecule Spectroscopy," Analytical Chemistry, vol. 78, No. 17, Sep. 1, 2006, pp. 6238-6245.
Bharadwaj et al., "Nanoplasmonic enhancement of single-molecule fluorescence," Nanotechnology 18 (2007), pp. 1-5.
Kappeler et al., "Field Computations of Optical Antennas," Journal of Computational and Theoretical Nanoscience, vol. 4, No. 3, 2007, pp. 686-691.
Esteban et al., "Simulation of optical near and far fields of dielectric apertureless scanning probes," Nanotechnology 17 (2006), pp. 475-482.
Ju et al., "Four-color DNA sequencing by synthesis using cleavable fluorescent nucleotide reversible terminators," Proceedings of the National Academy of Sciences of the United States of America, Dec. 26, 2006, vol. 103, No. 52, pp. 19635-19640.
Japanese Office Action issued in Japanese Patent Application No. JP 2008-093275 dated Apr. 27, 2010.

*Primary Examiner* — Roberto Velez
(74) *Attorney, Agent, or Firm* — McDermott Will & Emery LLP

(57) ABSTRACT

The present invention provides a nucleic acid analyzing apparatus which achieves highly accurate analytical ability even in single molecule DNA analysis. The nucleic acid analyzing apparatus detects locations of fluorescent bright spots in image information about light emission, deletes defective bright spots, and thereby creates intensity trace data about proper bright spots.

6 Claims, 18 Drawing Sheets

NUCLEIC ACID ANALYZING APPARATUS

BACKGROUND OF THE INVENTION

1. Field of the Invention

The present invention relates to a nucleic acid analyzing apparatus and, more particularly, to a nucleic acid analyzing apparatus such as a genetic tester/analyzer which observes fluorescence produced, for example, on a reaction device for single molecule DNA analysis and conducts analysis based on luminance of fluorescent bright spots.

2. Background Art

Regarding a typical nucleic acid analyzing method, Non-Patent Document 1 proposes a method which traps, molecule by molecule, a DNA test piece to be analyzed, on a DNA probe formed on a substrate surface, elongates bases one at a time, detects the bases using fluorometry, and thereby determines a base sequence.

Available analytical methods for reaction devices include a microarray analysis method which uses a semiconductor chip. The method has been used in the field of gene expression analysis. To detect a targeted gene polymorphism known as an SNP, the method hybridizes a target with a reaction spot to which a probe has been adsorbed in advance. Expression of the gene polymorphism can be optically detected if DNA to be linked is marked with fluorescent molecules.

The conventional microarray analysis method and the like shoot images of fluorescent bright spots produced in a specimen and perform gene analysis using resulting image information. Image shooting and image processing are indispensable to the present field and are important processes which govern reliability of specimen analysis results.

In particular, in the field or the like of multiple molecule fluorescent DNA detection by a microarray analysis method which uses a semiconductor chip, using a CCD or the like which is a two-dimensional imaging element as an optical detection element, reaction spots on a DNA chip can be associated easily with pixels in an output image by bringing the reaction spots on a DNA chip into one-to-one correspondence with CCD pixels or by using a reduction/binning function of a CCD camera. Consequently, in the field of conventional gene analysis apparatus, images and other data acquired by an imaging element can be used without preprocessing.

For example, Patent Document 4 proposes a method for performing fluorescent detection using a small number of pixels by placing image magnification of a focusing/image-forming optical system and a pixel pitch of a two-dimensional sensor in a predetermined relationship when reaction devices are arranged at equal intervals.

[Patent Document 1] JP Patent Publication (Kokai) No. 2006-337245 A
[Patent Document 2] JP Patent Publication (Kokai) No. 2007-10325 A
[Patent Document 3] JP Patent Publication (Kokai) No. 2004-101376 A
[Patent Document 4] JP Patent Publication (Kokai) No. 2007-322185 A
[Non-Patent Document 1] P.N.A.S. 2003, Vol. 100, pp. 3960-3964
[Non-Patent Document 2] Physical Review Letters 2006, 96, pp. 113002-113005
[Non-Patent Document 3] Anal. Chem. vol. 78, 6238-6245
[Non-Patent Document 4] Nanotechnology, 2007, vol. 18, pp. 044017-044021
[Non-Patent Document 5] J. Comput. Theor. Nanosci. 2007, vol. 4, pp. 686-691
[Non-Patent Document 6] Nanotechnology, 2006 vol. 17, pp. 475-482
[Non-Patent Document 7] P.N.A.S. 2006, Vol. 103, pp. 19635-19640

SUMMARY OF THE INVENTION

Recent nucleic acid analyzing apparatus, which have been put into practical use in a wide range of gene analyses including food analysis, medical analysis, authentication analysis, and academic analysis, require highly accurate analytical ability.

With analytical methods which use semiconductor chips, reaction spots where reactions take place have been minimized to analyze a larger number of reactions in parallel, and a single molecule DNA sequencer which uses single molecule fluorescence—the ultimate form of minimization—is becoming the mainstream of the next generation DNA sequencing. To observe such minimized areas, it is necessary to do high-magnification, high-sensitivity shooting of bright spots using a magnifying optical system and perform software-based image preprocessing for correction of optical distortion and misalignment. Conventional techniques which simply shoot reaction devices and detect fluorescent reactions in resulting images based on density of pixels cannot provide high accuracy results.

Also, for nucleic acid analyzing apparatus, amounts of information to be processed by gene analysis have been increasing explosively due to recent technological innovation. For example, gene analysis methods exemplified by the microarray analysis method analyze several hundred to several thousand specimens at a time, requiring high-quality images which can keep up with such amounts of information. Thus, CCD (Charge-Coupled Device) image sensor elements and CMOS (Complementary Metal Oxide Semiconductor) image sensor elements most commonly used in nucleic acid analyzing apparatus to detect fluorescence on reaction devices are being improved in image quality and sensitivity day by day, resulting in increases in the amount of collected data accordingly. For example, the pixel count of generally available CCD elements was on the order of 1 to 2 million pixels at the most in the latter half of the '90s, but has increased approximately tenfold to 10 to 20 million pixels in 2007. Furthermore, regarding resolutions of commercially available industrial CCD cameras, since sensitivity improvements and noise reductions have enabled quantization at high resolutions, resolutions of approximately 14 to 16 bits have become dominant now instead of previous resolutions of approximately 8 to 10 bits.

Consequently, nucleic acid analyzing apparatus are also required to be able to conduct analysis using high-quality images. Specifically, along with increases in the amount of data due to image quality improvements, reductions in unit size of reaction spots to be shot, and increases in the number of reaction spots, it has become necessary to be able to analyze individual spots accurately from a huge amount of data contained in each image. Also, it is required to distinguish bright spots accurately in spite of the difficulty to acquire an image by putting reaction spots into one-to-one correspondence with pixels of an imaging element.

Thus, it is necessary to pick out necessary bright-spot information. This is because if an image of light emission is shot as it is, the image will contain non-light-emitting reaction spots and a background. As a means of collecting only necessary bright spots, the use of a one-dimensional sensor is proposed by Patent Document 1 (listed above), but the proposed technique is not specialized in single molecule DNA analysis, and is required to physically move the one-dimensional optical sensor to a targeted bright spot, increasing the size of the analyzing apparatus and requiring time for processing.

Also, it is necessary to delete defective bright spots because, after the necessary bright-spot information is picked out, the image may contain light emission due to dirt, indistinct bright spots with low luminance, noise other than bright spots, and the like.

The present invention has been made in view of the above circumstances and provides a nucleic acid analyzing apparatus which achieves highly accurate analytical ability even in single molecule DNA analysis and the like.

To achieve the above object, the present invention provides a nucleic acid analyzing apparatus equipped with an imaging element for use to image a reaction device, comprising: preliminary shooting means for shooting the reaction device using the imaging element; bright-spot detection means for transmitting data generated by A/D conversion of an entire area of an image obtained by preliminary shooting to an analyzing computer via a communications control interface in a camera unit, detecting only bright-spot coordinates of the reaction device in the data, and storing the bright-spot coordinates as first binning positions; defective bright-spot discriminating means for discriminating and deleting any defective bright spot from the first binning positions, calculating only predetermined bright-spot information, and storing the calculated bright-spot information as second binning positions, in the analyzing computer; binning-position information transfer means for transmitting information about the second binning positions from the analyzing computer back to a camera control MPU via an apparatus control computer and the communications control interface in the camera unit; and main shooting means for collecting images by varying a drive signal to selectively collect only imaging-element information included in the second binning positions.

In this case, the imaging element may be a solid-state imaging element.

Also, a one-dimensional photosensor may be used as the imaging element to observe fluorescent bright spots on the reaction device by scanning the reaction device.

Also, the present invention provides a nucleic acid analyzing apparatus equipped with an imaging element for use to image a reaction device, comprising: preliminary shooting means for shooting the reaction device using the imaging element; bright-spot detection means for transmitting data generated by A/D conversion of an entire area of an image obtained by preliminary shooting to an analyzing computer via a communications control interface in a camera unit, detecting only bright-spot coordinates of the reaction device in the data, and storing the bright-spot coordinates as first binning areas at unequal intervals; defective bright-spot discriminating means for discriminating and deleting any defective bright-spot from the first binning areas, calculating only predetermined bright-spot information, and storing the calculated bright-spot information as second binning areas, in the analyzing computer; binning-area information transfer means for transmitting information about the second binning areas from the analyzing computer back to a camera control MPU via an apparatus control computer and the communications control interface in the camera unit; main shooting means for selectively summing a plurality of pieces of imaging-element information collected near bright spots calculated as the binning areas and converting the summed imaging-element information into digital values; and main shooting means for collecting images by varying a drive signal to selectively collect only imaging-element information included in the second binning areas.

In this case, the binning areas may be preset in a storage device.

Also, the present invention provides a nucleic acid analyzing apparatus equipped with an imaging element for use to image a reaction device, comprising: main shooting means for shooting the reaction device using the imaging element; bright-spot detection means for transmitting data generated by A/D conversion of an entire area of an image obtained by main shooting to an analyzing computer via a communications control interface in a camera unit, detecting only bright-spot coordinates of the reaction device in the data; defective bright-spot discriminating means for discriminating and deleting any defective bright-spot from the detected bright-spot coordinates and calculating only predetermined bright-spot information, in the analyzing computer; multi-area bright-spot information integrating means for integrating bright-spot information over a plurality of areas in the bright-spot coordinates calculated by the bright-spot detection means and the defective bright-spot discriminating means, in the analyzing computer; and intensity trace data collecting means for collecting changes in the integrated bright-spot information with time, analyzing a change pattern of a bright spot, and thereby determining whether the bright spot is a desired one, in the analyzing computer.

By performing image processing including detection of bright spots and discrimination of defective bright spots, the present invention can achieve highly accurate analytical ability even in single molecule DNA analysis.

DESCRIPTION OF SYMBOLS

Figure 1:
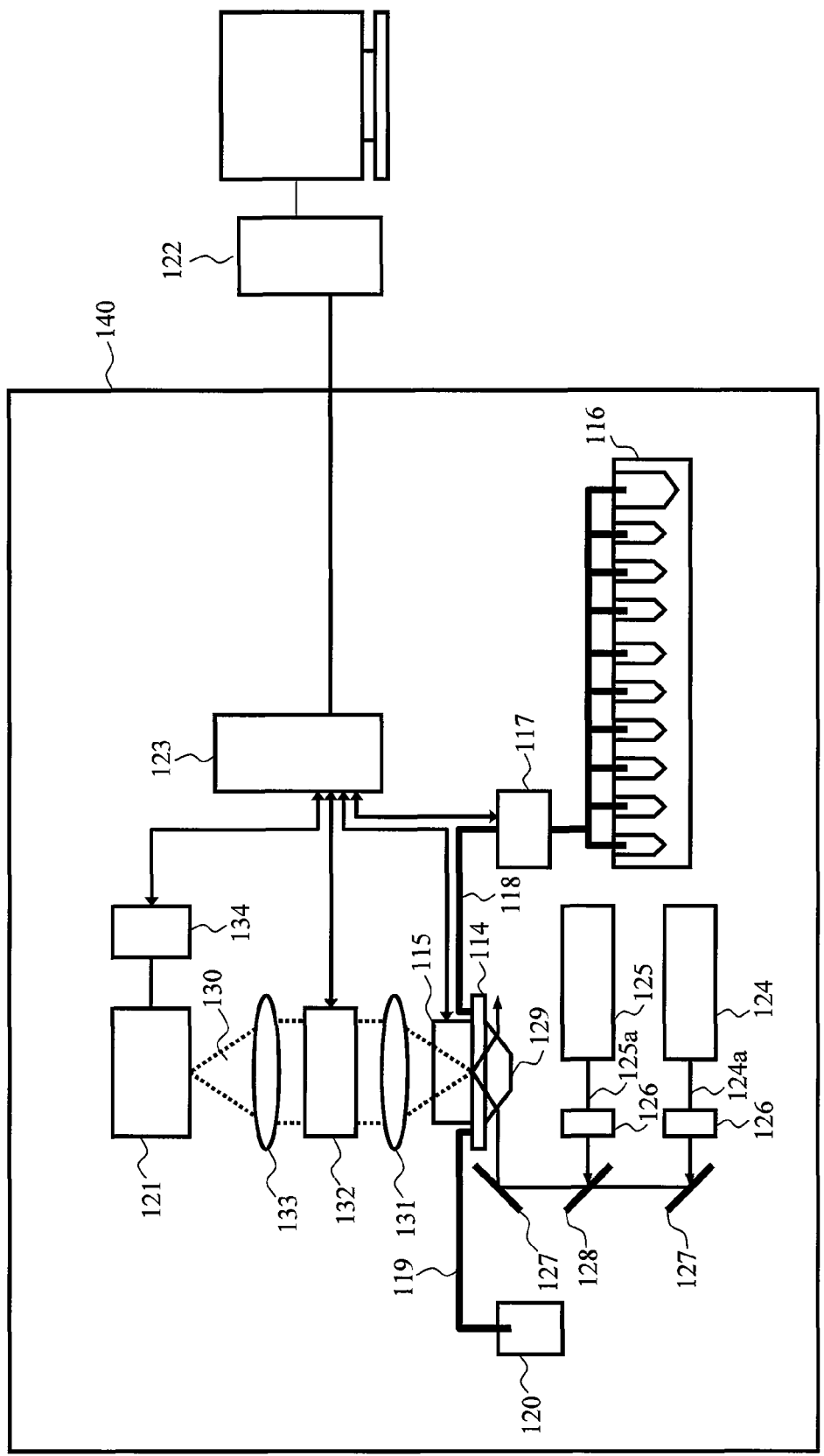
FIG. 1 is a diagram illustrating a configuration of an analyzing apparatus according to first to third embodiments.

114 . . . Reaction device
115 . . . Temperature control unit
116 . . . Reagent repository unit
117 . . . Dispensing unit
118 . . . Liquid-delivery tube
119 . . . Waste tube
120 . . . Waste container
121 . . . Two-dimensional sensor camera
122 . . . Analyzing computer
123 . . . Apparatus control computer
124 . . . YAG laser device
124a . . . YAG laser beam
125 . . . Ar laser device
125a . . . Ar laser beam
126 . . . Quarter-wave plate
127 . . . Mirror
128 . . . Dichroic mirror
129 . . . Prism
130 . . . Fluorescence
131 . . . Condenser lens
132 . . . Filter unit
133 . . . Image-forming lens
134 . . . Two-dimensional sensor camera controller
140 . . . Analyzer
200 . . . Camera unit
201 . . . Camera control MPU
202 . . . Main storage unit
203 . . . Solid-state imaging element
204 . . . A/D converter
205 . . . Communications control interface
206 . . . Apparatus control computer
207 . . . Vertical and horizontal drive signals
208 . . . Communications bus
301 . . . Solid-state imaging element unit
302 . . . Combined light-receiving and vertical transfer element
303 . . . Mechanical shutter
304 . . . φV signal
305 . . . φH signal
306 . . . A/D converter
307 . . . ADCK signal
308 . . . Digital value
309 . . . RCK signal
311 . . . Image-forming lens
312 . . . Horizontal transfer element
313 . . . Charge/voltage converter
314 . . . Vertical direction
315 . . . Horizontal direction
316 . . . Fluorescence
401 . . . Remove unnecessary electric charge
402 . . . Main shooting
403 . . . Detect bright spots
404 . . . Discriminate defective bright spots
405 . . . Integrate data over bright-spot areas
406 . . . Create intensity trace data
407 . . . Store data
408 . . . All fields of view processed?
409 . . . Finish collection
503 . . . Combined light-receiving and vertical transfer element
504 . . . φV signal
505 . . . φH signal
506 . . . RCK signal
507 . . . Vertical direction
508 . . . Horizontal direction
509 . . . Horizontal transfer element
510 . . . Charge/voltage converter
511 . . . Charge voltage
901 . . . Remove unnecessary electric charge
902 . . . Preliminary shooting
903 . . . Detect bright spots
904 . . . Discriminate defective bright spots
905 . . . Transfer binning position information
906 . . . Main shooting
907 . . . Create intensity trace data
908 . . . Store data
909 . . . All fields of view processed?
910 . . . Finish collection
1115 . . . Travel path of electric charge
1201 . . . Substrate
1202 . . . Reaction spot
1203 . . . Probe
1401 . . . Remove unnecessary electric charge
1402 . . . Preliminary shooting
1403 . . . Detect bright spots
1404 . . . Discriminate defective bright spots
1405 . . . Transfer binning area information
1406 . . . Main shooting (including integration)
1407 . . . Create intensity trace data
1408 . . . Store data
1409 . . . All fields of view processed?
1410 . . . Finish collection
1505 . . . Binning areas
1815 . . . Unnecessary pixel row

DETAILED DESCRIPTION OF THE PREFERRED EMBODIMENTS

Typical nucleic acid analyzing apparatus use full-frame or interline CCD, CMOS, or the like. Full-frame elements, which accumulate received light even during extraction of electric charges and A/D conversion, require a mechanical shutter. On the other hand, interline elements, which have a separate light-receiving element and horizontal/vertical transfer element, do not require a shutter. The present invention will be described by taking as an example a nucleic acid analyzing apparatus equipped with a full-frame CCD. Besides, the present invention is also applicable when a two-dimensional plane image is obtained by scanning in one or two directions using a light-detecting element such as a one-dimensional linear CCD or photomultiplier instead of using a two-dimensional imaging element as in the case of embodiments of the present invention.

First, in a first embodiment, a basic nucleic acid analyzing apparatus according to the present invention will be described below. Next, in a second embodiment, description will be given of a method for adapting a conventional ROI technique of extracting necessary information from light-receiving pixels to the first embodiment and a method for selectively reading bright spots by specifying bright-spot coordinates in advance. In a third embodiment, description will be given of a method for adapting summation of data over plural bright spots to the second embodiment and selectively reading bright spots by specifying coordinate areas in advance. In a fourth embodiment, description will be given of a method for adapting the scanning system according to Patent Document 1 to the present invention.

However, it should be noted that the embodiments described below are just a few examples of implementations of the present invention and are not intended to limit the technical scope of the present invention.

First Embodiment

A schematic configuration of a single molecule DNA sequencer as a nucleic acid analyzing apparatus according to the first embodiment is shown in a block diagram of FIG. 1. The present exemplary apparatus is a system based on plasmon resonance and includes an analyzer 140 and analyzing computer 122. Reaction in a reaction device 114 is observed by a two-dimensional sensor camera 121. The reaction device 114 is an optically transparent substrate, on which metal structures are placed in a grid arrangement. The metal structures are, for example, pairs of gold structures juxtaposed to each other or conical gold structures. Nucleic acid probes are fastened between each pair of metal structures or at the tips of the cones. Grooves or the like are cut in inner surfaces of a temperature control unit 115 to form a reaction chamber when the reaction device 114 is mounted. The reaction chamber holds a reaction solution on a surface of the reaction device 114 and the nucleic acid probe can be placed in the reaction solution. Also, a fluorescence-marked reagent can be supplied into the reaction solution.

To supply the reagent into the reaction device 114, the reagent stored in containers in a reagent repository unit 116 is dispensed by a dispensing unit 117 and delivered via a liquid-delivery tube 118. The supplied reagent has its temperature regulated by a temperature control unit 115 to facilitate reaction. When the reaction is completed, liquid waste is discharged to a waste container 120 via a waste tube 119.

The reagent in the reaction solution is trapped specifically by the nucleic acid probe which has formed a complex with a target nucleic acid, causing a sequencing reaction. To capture the sequencing reaction, fluorescent markers are excited by excitation light. Concretely, a YAG laser beam 124a or Ar laser beam 125a is emitted from a YAG laser device 124 or Ar laser device 125 according to excitation wavelength of a fluorescent dye. The emitted laser beam passes through a quarter-wave plate 126 which controls a laser polarization plane, has its optical axis unified by a mirror 127 and dichroic mirror 128, and is totally reflected by a prism 129. The laser beam totally reflected by the prism generates evanescent light on the side opposite an interface. The evanescent light is enhanced by a fluorescence enhancement field based on plasmon resonance of the metal structures. The enhanced evanescent light is used as excitation light for the fluorescent dye.

The fluorescent dye excited by the excitation light produces fluorescence 130. After being condensed by a condenser lens 131, the fluorescence 130 is transmitted through a filter unit 132 for noise removal. Then, the fluorescence 130 forms an image on an imaging plane of the two-dimensional sensor camera 121 via an image-forming lens 133. Image data resulting from shooting is transmitted to the analyzing computer 122 via a two-dimensional sensor camera controller 134 and apparatus control computer 123.

To perform the analysis-related operations described above, various units of the apparatus are controlled by the apparatus control computer 123 on instructions from the analyzing computer 122.

The analyzing computer is a typical personal computer or general-purpose computer or the like loaded with software which has a gene analysis function or sequence analysis function. The analyzing computer is not of particular importance here, and thus detailed description thereof will be omitted.

Figure 2:
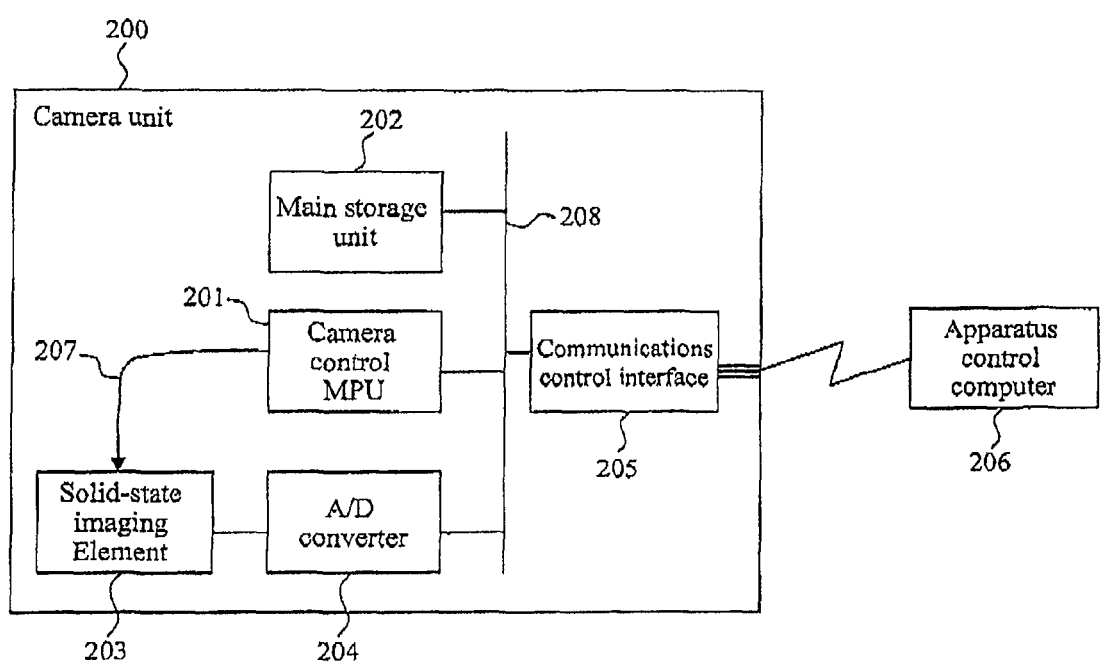
FIG. 2 is a diagram illustrating a camera incorporated in the analyzing apparatus according to the first to third embodiments.

A block diagram of a camera unit which is especially important for the present apparatus is shown in FIG. 2. The camera unit 200 includes a solid-state imaging element 203 which detects targeted fluorescence produced by gene elongation or other reaction, an A/D converter 204 which converts an electric signal from the solid-state imaging element 203 into a digital value, a camera control MPU 201 which controls the above components, a main storage unit 202 used in processing carried out by the MPU, and a communications control interface 205 which communicates with an apparatus control computer 206 and transmits bright-spot information or the like after A/D conversion. The components are interconnected via a communications bus 208. Also, vertical and horizontal drive signals 207 are generated by the camera control MPU 201 and supplied to the solid-state imaging element 203.

Figure 3:
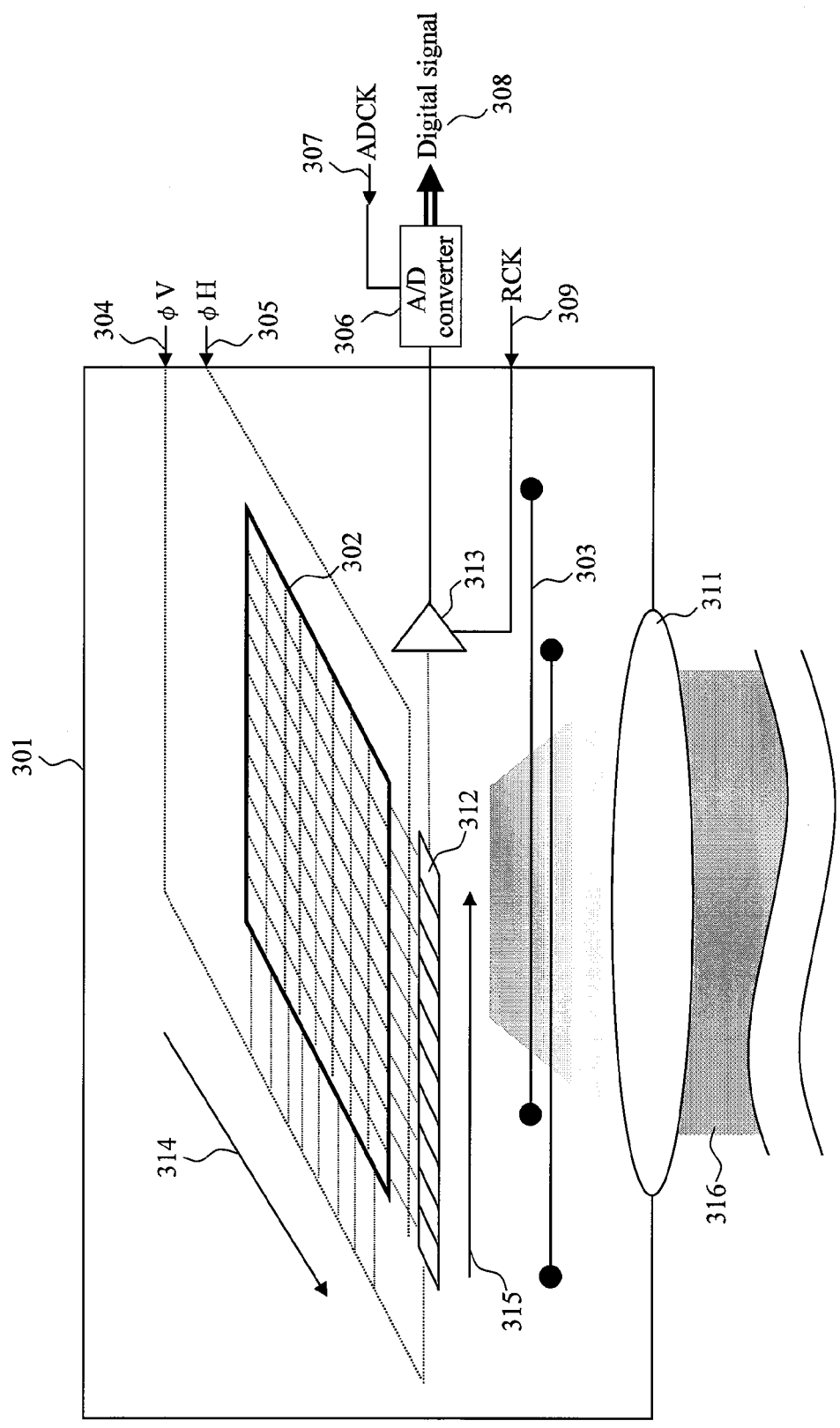
FIG. 3 is a diagram illustrating details of an imaging element used for the camera incorporated in the analyzing apparatus according to the first to third embodiments.

Next, to describe image shooting and image processing, a typical solid-state imaging element and its surroundings are shown in detail in FIG. 3.

In FIG. 3, the solid-state imaging element includes a combined light-receiving and vertical transfer element 302, horizontal transfer element 312, and charge/voltage converter 313. The combined light-receiving and vertical transfer element 302 receives fluorescence 316 from an observed object via an image-forming lens 311, accumulates the fluorescence 316 as electric charge, and moves the electric charge successively to adjacent elements in a vertical direction 314 in bucket-brigade fashion at a $\phi V$ signal 304.

The horizontal transfer element 312 is spatially and optically isolated from the combined light-receiving and vertical transfer element 302 so as not to receive light. The horizontal transfer element 312 is used only for the purpose of temporarily storing one or more lines of electric charge transferred in the vertical direction 314 from the combined light-receiving and vertical transfer element 302 and transferring the electric charge in a horizontal direction 315 in sequence. The electric charge transferred to a vertical end of the combined light-receiving and vertical transfer element 302 is eventually transferred to the horizontal transfer element 312 and transferred in the horizontal direction 315 in sequence at a $\phi H$ signal 305. The electric charge transferred in the horizontal direction 315 is converted into voltage in sequence beginning at the end by the charge/voltage converter 313. Subsequently, the voltage is converted by an A/D converter 306 into a digital signal and consequently into digital values 308.

An RCK signal 309 is used to remove the electric charge transferred to the charge/voltage converter 313. When the signal is given, the electric charge accumulated in the charge/voltage converter is cleared and consequently conversion produces zero voltage. An ADCK signal 307 can be used to control whether the charge/voltage converter 313 will convert electric charge. That is, when the electric charge at the location of a targeted bright spot is stored in the charge/voltage converter 313, if an ADCK signal 307 is given, quantity of charge which has been converted into voltage is further converted into the digital signal 308.

Figure 4:
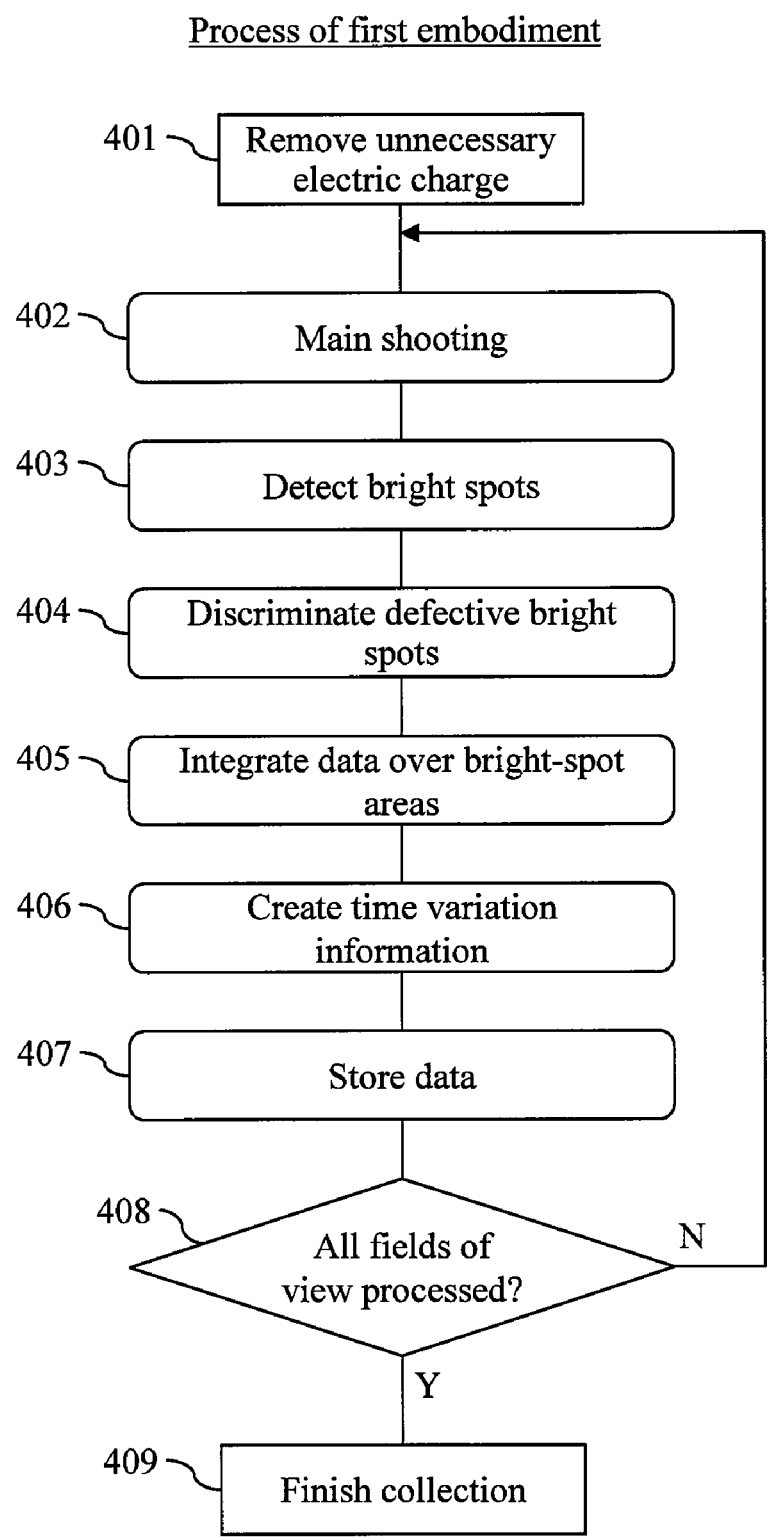
FIG. 4 is a flowchart of a data collection method performed on the analyzing apparatus according to the first embodiment.

Next, to describe image shooting procedures according to the present embodiment, FIG. 4 shows a flowchart of image shooting with the solid-state imaging element according to the present embodiment. The subject of actions in processes in the flowchart is the camera control MPU 201 shown in FIG. 2.

First, in Step 401, the camera control MPU 201 performs initialization to remove unnecessary electric charge. At an initial stage, any unnecessary electric charge, which may be accumulated in the combined light-receiving and vertical transfer element, needs to be removed. This operation is a charge removal operation in a camera which uses a typical solid-state imaging element, and thus detailed description thereof will be omitted.

In Step 402, the camera control MPU 201 performs a main shooting process. While hybridization is carried out on the reaction device, it is necessary to continue shooting the reaction device to observe time variation. The camera control MPU 201 directs a laser beam serving as excitation light at the reaction device, opens the mechanical shutter, thereby exposing the reaction device, converts all the electric charge accumulated as a result of the exposure into voltage, performs A/D conversion of the voltage, and transfers luminance information about all the pixels to the computer in sequence. The procedures from the exposure to the A/D conversion are typical procedures for cameras equipped with a solid-state imaging element, but they are essential to understanding the basic concepts of the present invention, and thus will be described in detail below with reference to FIG. 5.

Figure 5:
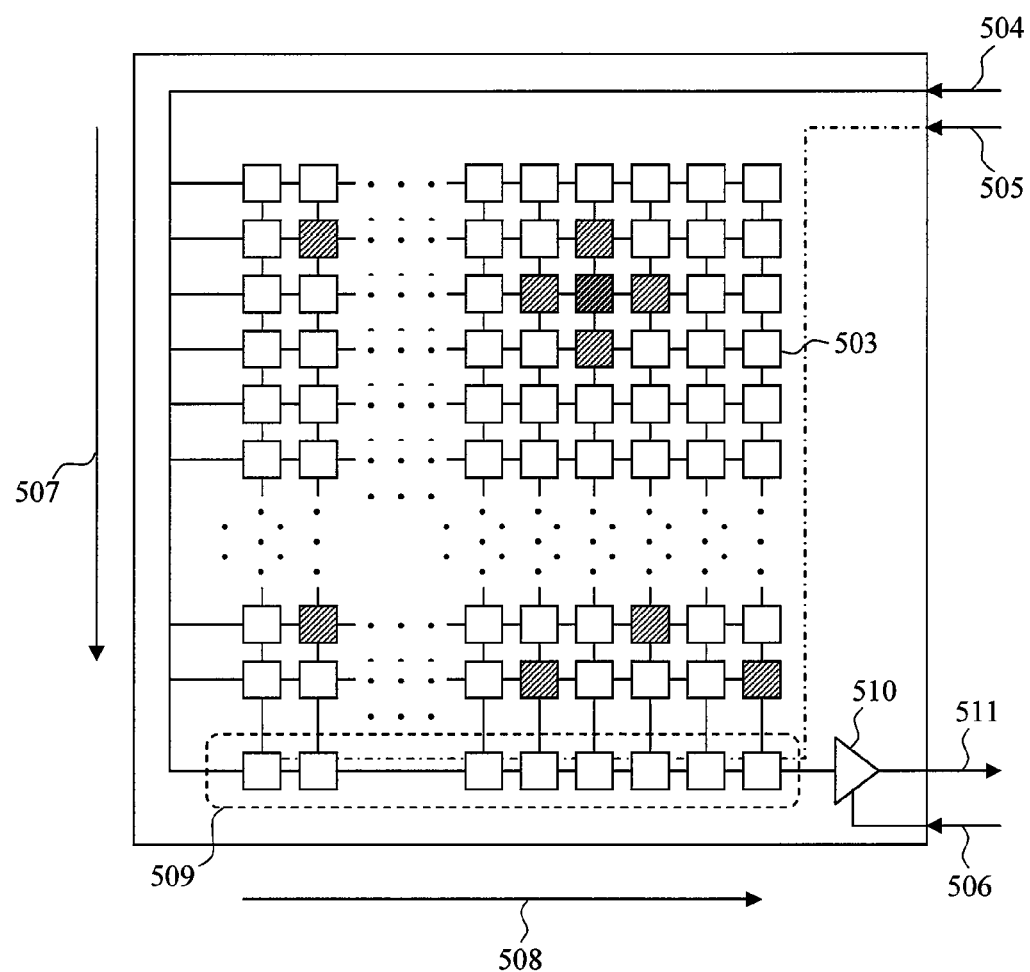
FIG. 5 is a diagram illustrating a solid-state imaging element drive method according to the first embodiment.
Figure 6:
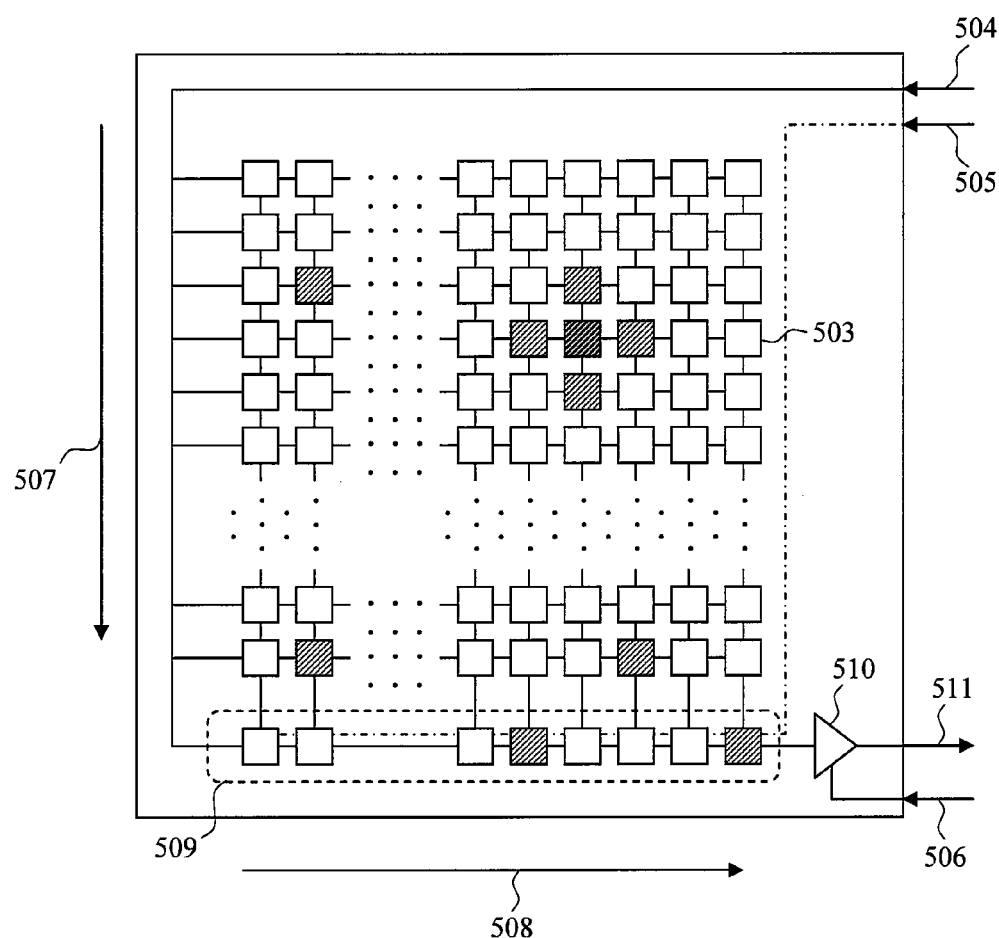
FIG. 6 is a diagram illustrating the solid-state imaging element drive method according to the first embodiment.
Figure 7:
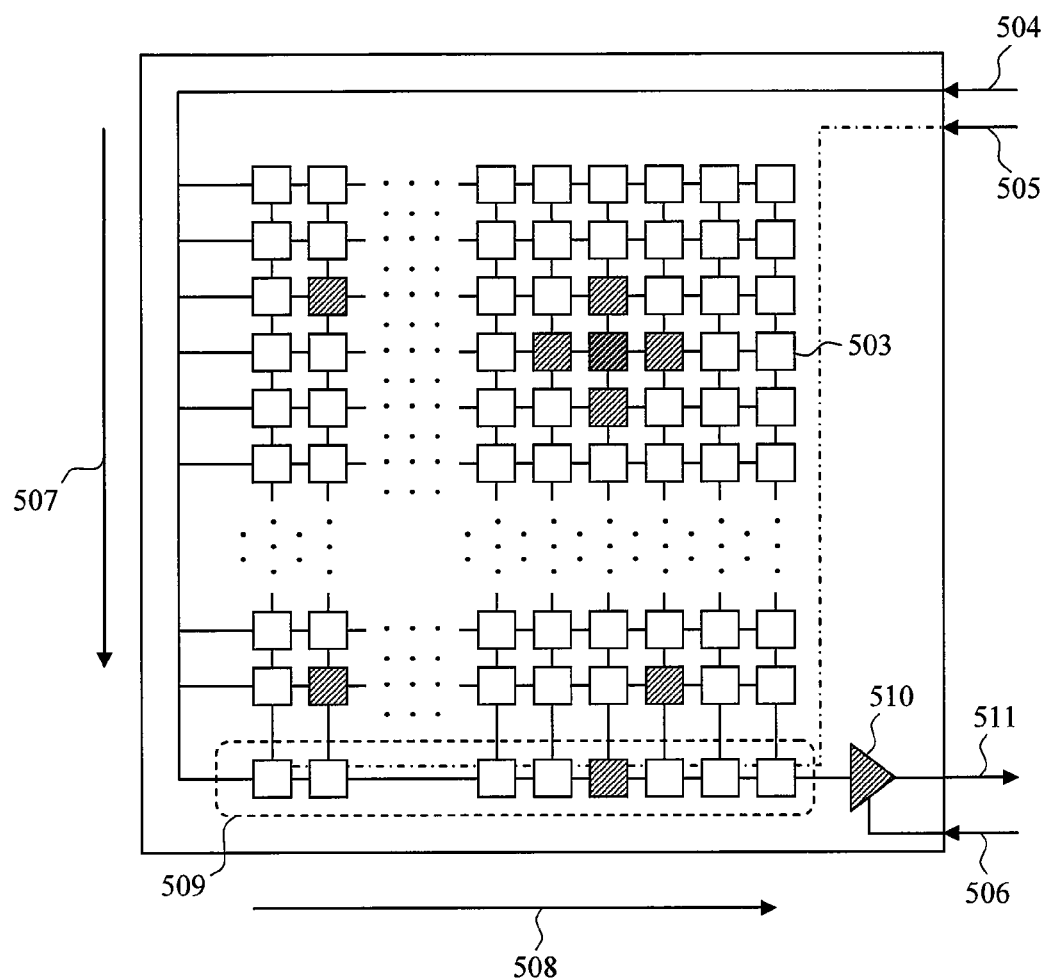
FIG. 7 is a diagram illustrating the solid-state imaging element drive method according to the first embodiment.

FIG. 5 illustrates the combined light-receiving and vertical transfer element 302 in detail, wherein shaded areas represent electrically charged elements which have just been exposed. In the following description, the subject of actions is the camera control MPU 201 shown in FIG. 2. First, the camera control MPU 201 transfers the electric charge stored in each pixel from a combined light-receiving and vertical transfer element 503 to a horizontal transfer element 509. That is, when a φV signal 504 is given, the electric charge stored in the combined light-receiving and vertical transfer element 503 is transferred vertically in bucket-brigade fashion. A state of electric charge after one pulse of the φV signal 504 is given is shown in FIG. 6. The electric charge moved to the horizontal transfer element is further transferred in a horizontal direction 508 at a φH signal 505. A state of electric charge after one pulse of the φH signal 505 is given is shown in FIG. 7. Moving in the horizontal direction 508, the electric charge is inputted in a charge/voltage converter 510, which consequently outputs a charge voltage 511. As the voltage signal undergoes A/D conversion, a luminance value of the pixel is obtained in the form of a digital value. After the luminance value is obtained through the A/D conversion of the voltage, the electric charge in the charge/voltage converter 510 is removed at an RCK signal 506. Similarly, a next pulse of the φH signal is given, the voltage signal undergoes A/D conversion, an RCK signal 506 is given after a luminance value is obtained. In this way, when φH signal pulses corresponding to the number of pixels in the horizontal direction 508 are given, digital luminance values for one line in the horizontal direction 508 are obtained. Also, φV signal 504 inputs and φH signal inputs are given alternately, charge/voltage conversion is repeated, and thereby luminance values of all the pixels are collected. The operation of collecting data on all the pixels in this way is referred to hereinafter as full frame collection.

Figure 8:
FIG. 8 is a diagram showing an example of an image of fluorescent bright spots shot by the analyzing apparatus according to the first embodiment.

The digital values of all the pixels thus obtained are assembled to produce a two-dimensional image. An example of an image obtained by the above method is shown in FIG. 8. Apart from this method, Patent Document 1 proposes a method for scanning only a necessary part by a one-dimensional optical sensor to obtain information about only targeted bright spots.

Returning to FIG. 4, after the main shooting is completed, the camera control MPU 201 makes the analyzing computer 122 calculate coordinates of the location of each fluorescent bright spot in Step 403. The process of calculation generally uses a method which detects a peak position of bright-spot luminance using a threshold, finds a Gaussian approximation of three to five pixels around the peak position, and calculates a bright-spot peak position at a sub-pixel level. This method of integration allows coordinates of a given bright spot to be detected accurately even if there is no exact one-to-one correspondence between the reaction spots on the reaction device and pixels of the solid-state imaging element.

In Step 404, the camera control MPU 201 makes the analyzing computer 122 perform predetermined processes: delete defective bright spots, detect proper bright spots, and exclude information about the defective bright spots from information to be collected. For example, when plural reaction spots are located extremely close to each other and bright-spot luminance falls outside a normal bright-spot luminance range determined in advance according to the purpose of analysis, a process such as proposed in Patent Document 2 is available. The process involves determining unnecessary spots in advance and identifying specific spots easily in an optical image. Also, in detecting bright spots, a process such as proposed in Patent Document 3 is available. The process involves setting a threshold according to magnitude of luminance, determining reaction spots which need to be collected, and detecting proper bright spots. Procedures of these processes are not of particular importance to the present invention, and thus detailed description thereof will be omitted.

In Step 405, the camera control MPU 201 makes the analyzing computer 122 integrate bright-spot information over plural areas as required. In the process of integration, the camera control MPU 201 integrates luminance information over an area of desired shape such as a coordinate area determined by a calculation of two's multiples or a predetermined calculation method, examples of which include a coordinate area equal to or larger than a threshold given by the Gaussian approximation calculated in Step 403. This method of integration allows the total amount of fluorescence of a given bright spot to be detected accurately even if there is no exact one-to-one correspondence between the reaction spots on the reaction device and pixels of the solid-state imaging element.

In Step 406, the camera control MPU 201 makes the analyzing computer 122 create intensity trace data of each fluorescent bright spot. The intensity trace data is collected to indicate how the bright-spot luminance calculated in the process up to Step 405 changes with time. The intensity trace data is collected and a variation pattern is analyzed in order to determine whether or not the bright spot is a desired one. With typical fluorescent dyes, bright spots light up once and then quench in a very short time. Any bright spot that shows another pattern such as remaining lit or lighting up more than once is regarded to be a defective bright spot.

In this way, the camera control MPU 201 makes the analyzing computer 122 create the intensity trace data of each fluorescent bright spot in Step 406.

In Step 407, the camera control MPU 201 stores results in a storage device of the analyzing computer.

Finally, if there is more than one field of view, the camera control MPU 201 goes from Step 408 to Step 402 to repeat processes until observations in all the fields of view are complete. When observations in all the fields of view are finished, the collection is finished (Step 409).

The above has been a flow of a fluorescence signal collection method for the nucleic acid analyzing apparatus according to the first embodiment.

As described above, the nucleic acid analyzing apparatus according to the present invention detects locations of fluorescent bright spots in image information about light emission, deletes defective bright spots, and thereby creates intensity trace data about proper bright spots without increase in the scale of the apparatus. Consequently, the present invention can achieve highly accurate analytical ability even in single molecule DNA analysis.

Second Embodiment

With the nucleic acid analyzing apparatus according to the first embodiment, all images containing a background and noises are captured, charge/voltage conversion and A/D conversion of all pixels are carried out, and all resulting data is transferred to the computer while shooting is continued during all hybridization, and thus the first embodiment is useful when pixel count is relatively small.

On the other hand, to allow for higher-quality images and longer light-emission observations, a second embodiment supports data processing capacity and image transfer capacity of a computer as high as tens of frames per second. This takes into consideration not only loads on the computer which performs a series of processes including the process of distinguishing bright-spot information in such heavy data volumes, but also loads on a transfer path used subsequently to transfer the information.

Thus, the second embodiment is intended to improve image processing speed and image transfer speed based on the first embodiment.

Image shooting procedures according to the present embodiment will be described with reference to FIG. 9.

In Step 901, the camera control MPU 201 performs initialization to remove any unnecessary electric charge, which may be accumulated at an initial stage as in the case of typical cameras. For that, the camera control MPU 201 gives as many $\phi V$ signal pulses as there are vertical pixels and as many $\phi H$ signal pulses as there are horizontal transfer elements, as in the case of the first embodiment.

In Step 902, the camera control MPU 201 does preliminary shooting to detect only necessary bright-spot coordinates beforehand in preparation for main shooting (described later). The camera control MPU 201 carries out hybridization on the reaction device, directs a laser beam serving as excitation light at the reaction device, opens the mechanical shutter, thereby exposing the reaction device, converts all the electric charge accumulated as a result of the exposure into voltage, and performs A/D conversion of the voltage. To detect bright-spot coordinates, the camera control MPU 201 collects pixels full-frame for high resolution by reading one frame per pixel as in the case of the first embodiment, and transmits the collected image to the analyzing computer 122 via the communications control interface 205 and apparatus control computer 206. The image is used only for the purpose of checking the locations of bright spots, and needs to have the highest resolution available with the camera. Regarding the number of shots, one shot is enough to detect bright spots, and a few shots are sufficient even when averaging for noise reduction is taken into consideration.

After the preliminary shooting is completed, the camera control MPU 201 makes the analyzing computer 122 calculate coordinates of the location of each fluorescent bright spot in Step 903. The analyzing computer 122 detects targeted bright spots in the collected image, lists pixel location coordinates, and stores the locations as first binning positions.

In Step 904, the analyzing computer 122 picks out and deletes defective bright spots which should not be collected. The bright spots determined to be held back from being collected are deleted from the first binning positions. The binning positions after the modification are stored as second binning positions. To detect bright-spot locations, any of conventional bright-spot detection methods is available for use. For example, when plural reaction spots are located extremely close to each other and bright-spot luminance falls outside a normal bright-spot luminance range determined in advance according to the purpose of analysis, a process such as proposed in Patent Document 2 is available. The process involves determining unnecessary reaction spots in advance and identifying specific spots easily in an optical image. Also, in detecting bright spots, a process such as proposed in Patent Document 3 is available. The process involves setting a threshold according to magnitude of luminance, determining reaction spots for data collection, and detecting proper bright spots. Procedures of these processes are not of particular importance to the present invention, and thus detailed description thereof will be omitted.

In Step 905, information about the second binning positions calculated by the analyzing computer 122 is transmitted back to the camera control MPU 201 via the apparatus control computer 206 and via the communications control interface 205 in the camera unit.

In Step 906, the camera control MPU 201 does main shooting. While hybridization is carried out on the reaction device, it is necessary to continue shooting the reaction device to observe time variation. The camera control MPU 201 directs a laser beam serving as excitation light at the reaction device and opens the mechanical shutter, thereby exposing the reaction device. The camera control MPU 201 controls the $\phi V$ signal and $\phi H$ drive signal such that electric charge will be collected from the pixels only at the binning positions detected in advance by the preliminary shooting. The electric charge of targeted bright spots is subjected to charge/voltage conversion and A/D conversion, and bright-spot information about only necessary bright spots is transferred as digital values to the computer in sequence. Electric charge of bright spots other than the targeted bright spots are removed. Consequently, in the main shooting, information about only the necessary bright spots are collected and transferred. When required exposure time elapses, the camera control MPU 201 closes the mechanical shutter and finishes the exposure. After the exposure is finished, only the coordinates represented by information about the binning positions detected in the preliminary shooting step in advance are subjected to charge/voltage conversion and A/D conversion.

Figure 10:
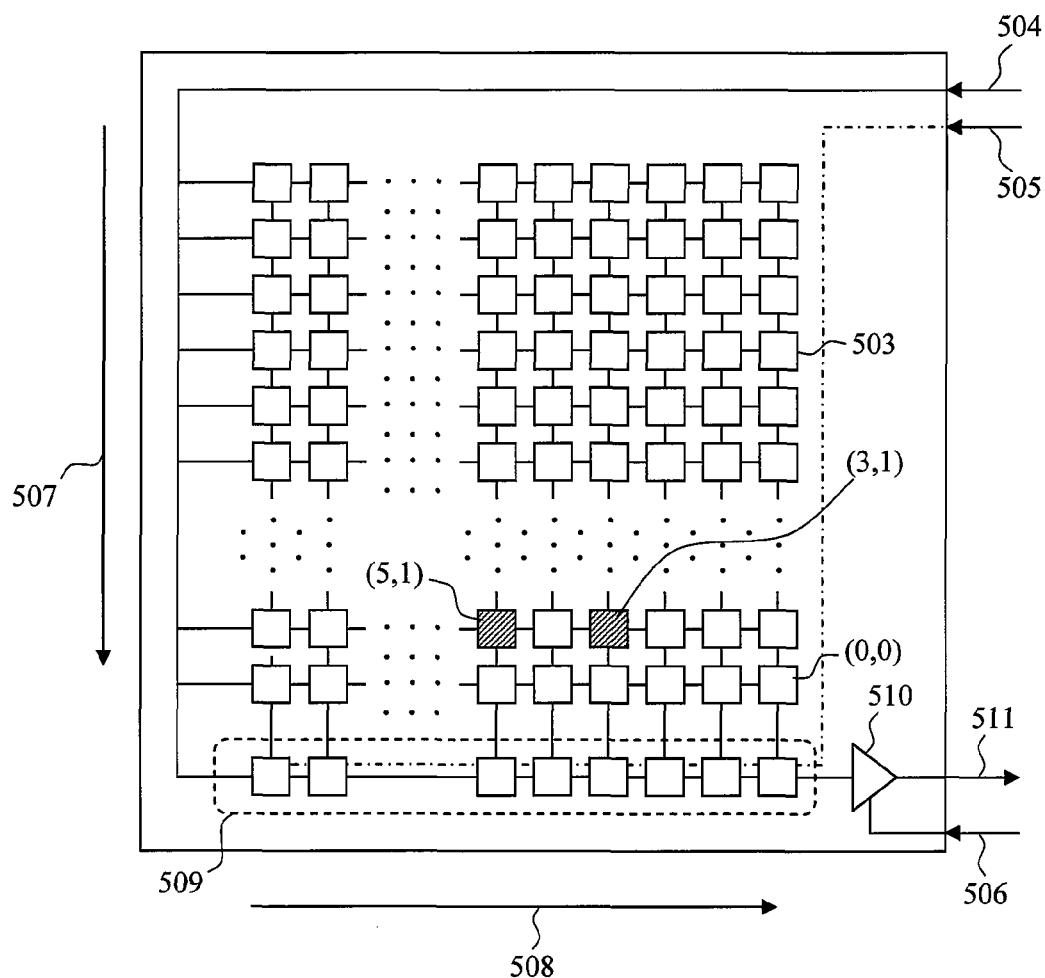
FIG. 10 is a diagram illustrating a solid-state imaging element drive method according to the second embodiment.
Figure 11:
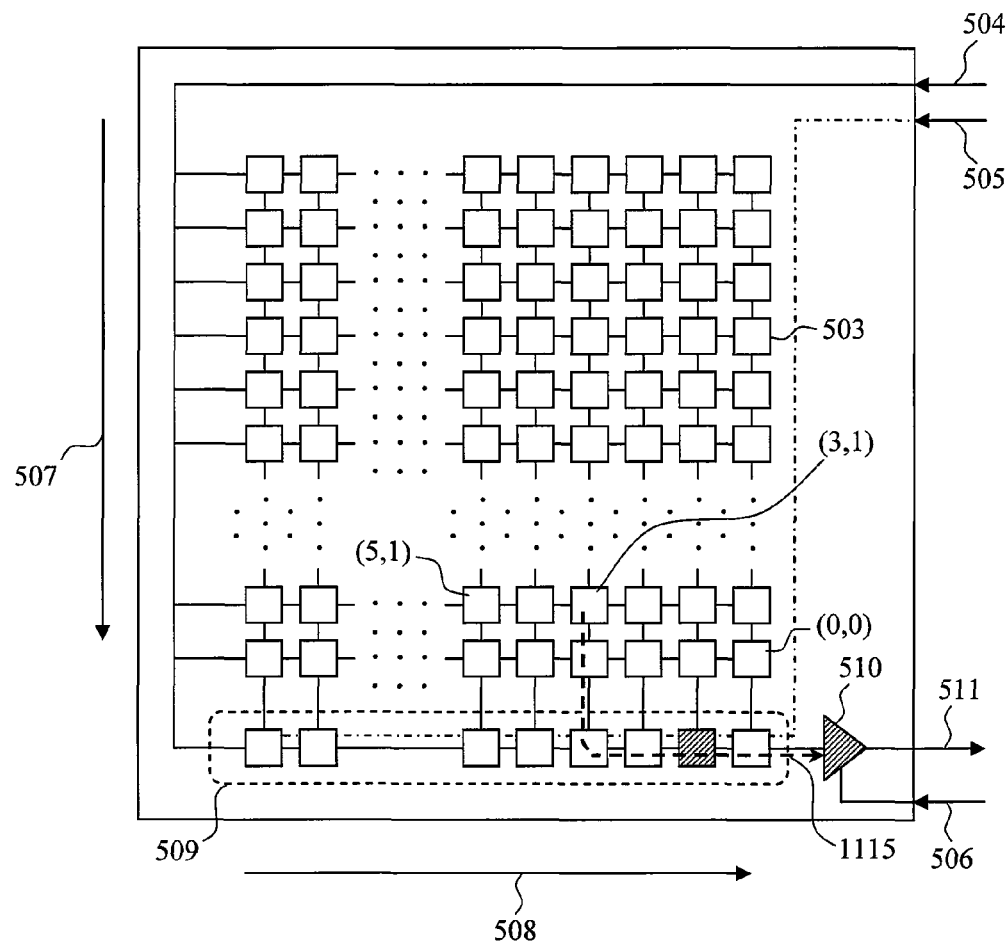
FIG. 11 is a diagram illustrating the solid-state imaging element drive method according to the second embodiment.

A concrete example of the operation of selectively collecting the pixels at targeted binning positions is shown in FIG. 10. In the combined light-receiving and vertical transfer element 503 shown in FIG. 10, origin coordinates (0, 0) are placed in lower right part of the figure and the bright-spot coordinates (x, y) closest to the origin are assumed to be located at (3, 1). If two pulses of the $\phi V$ signal 504 are given first and four pulses of the $\phi H$ signal 505 are given next, the electric charge at coordinates (3, 1) is inputted in the charge/voltage converter. State of electric charge which results after the above-mentioned numbers of pulses of the $\phi V$ signal 504 and $\phi H$ signal 505 are given is shown in FIG. 11. When the drive signals are given, the electric charge moves to the charge/voltage converter 510 via a travel path 1115 of electric charge. Only then are charge/voltage conversion and A/D conversion carried out.

If a bright spot to be acquired next is located at (5, 1), the electric charge at the coordinates will be subjected to charge/voltage conversion when two more pulses of the $\phi H$ signal 504 are given as shown in FIG. 11. Thus, charge/voltage conversion and A/D conversion are carried out after two pulses of the $\phi H$ signal 504 are given.

In Step 907, the camera control MPU 201 makes the analyzing computer 122 create intensity trace data of each fluorescent bright spot obtained by the main shooting.

Figure 9:
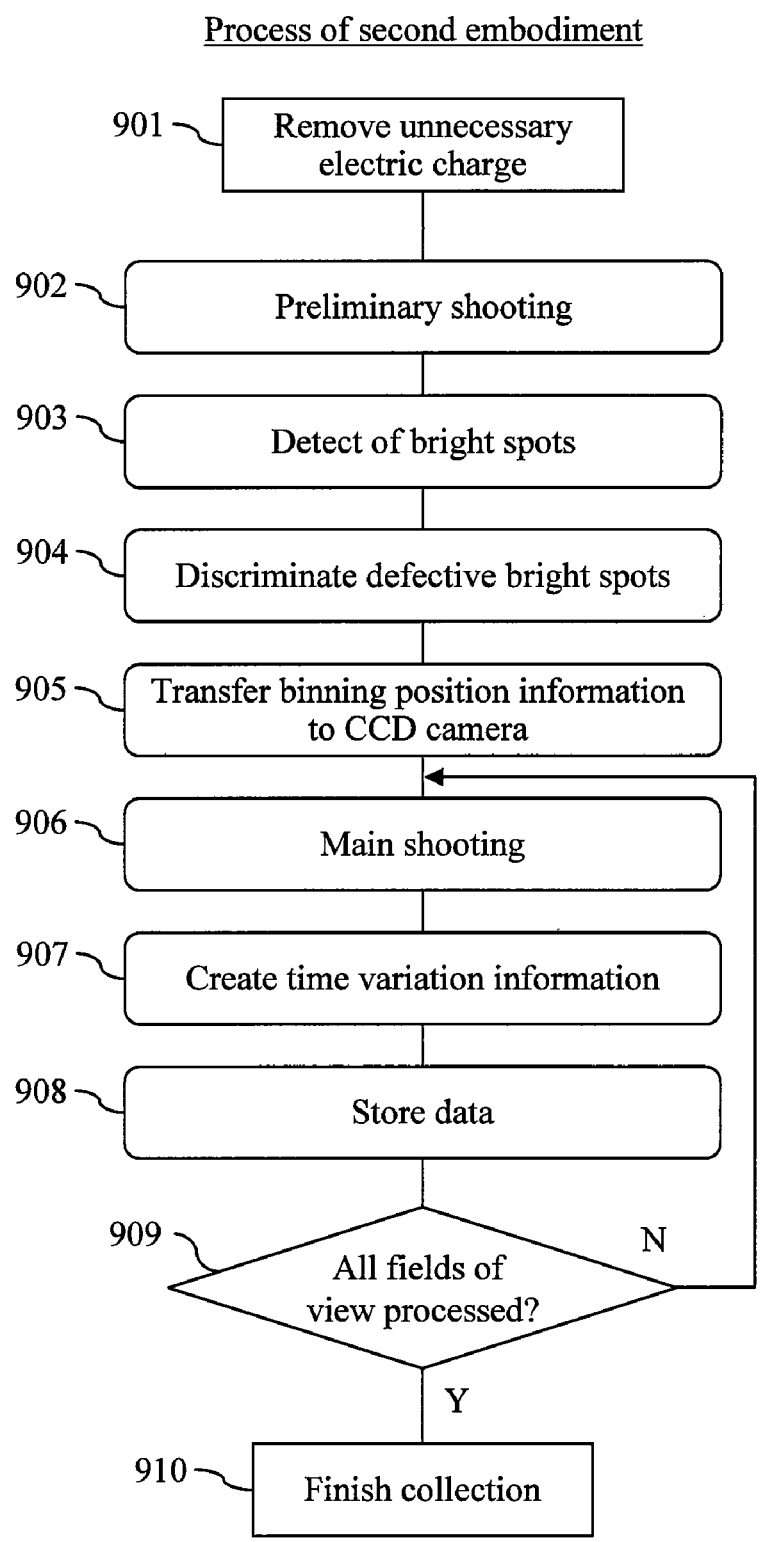
FIG. 9 is a flowchart of a data collection method performed on an analyzing apparatus according to a second embodiment.

Once the necessary fluorescent bright spots are selectively collected and results are obtained, the camera control MPU 201 stores the results in a storage device (not shown) in Step 908 of FIG. 9.

When the data has been stored, the camera control MPU 201 goes from Step 909 to Step 906 to repeat processes until observations in all the fields of view are complete. When observations in all the fields of view are finished, the collection is finished (Step 910).

Note that the present embodiment differs from the first embodiment in that, as described above, only necessary bright spots excluding the background and defective bright spots undergo data conversion and transfer during observation of the reaction device at the time of main shooting.

As described above, to accommodate processing and transfer of a huge amount of data carried out over an extended period of time, by identifying coordinate locations of necessary bright spots in advance, the present embodiment removes unnecessary areas without charge/voltage conversion or A/D conversion and carries out charge/voltage conversion and A/D conversion of only targeted bright-spot locations without high-accuracy alignment which is unavoidable with the binning method. Consequently, all the unnecessary information is removed from the acquired image information, reducing the amount of acquired data. Besides, since detection of bright spots and discrimination of defective bright spots are carried out only once at the time of preliminary shooting rather than for each field of view, image processing speed can be improved with increases in the number of fields of view for shooting.

Among conventional techniques in the field of camera systems, there is a technique which allows a region of interest (ROI) to be set in advance and selectively reads necessary information from part of a light-receiving pixel to improve processing speed. However, a typical camera allows only one ROI to be specified per exposure, and thus the technique is not applicable to nucleic acid analyzing apparatus which have to capture plural bright spots at a time.

Third Embodiment

In addition to a feature of the second embodiment, i.e., the feature of selectively collecting only necessary fluorescent bright spots, a third embodiment has the feature of summing bright-spot luminance values.

The third embodiment is intended to provide clearer images based on the second embodiment intended to speed up data processing.

The second embodiment makes it possible to collect a bright-spot luminance value from a targeted pixel quickly and easily. On the other hand, in applications to analyzing apparatus on which the present invention is focused, it is important to be able to easily distinguish content of images used for observation on a reaction device.

Thus, by advancing a conventional technique in the field of camera systems, namely, a binning technique which increases apparent sensitivity by adding up electric charges of a solid-state imaging element, the present embodiment uses a method for summing arbitrary predetermined areas on the imaging element during preliminary shooting using a method described later.

Generally, when obtaining the luminance of a bright spot, the method averages or sums a few pixels around the bright spot to absorb positional error between pixel and bright spot and reduce noise. By assuming that reaction spots on the reaction device are lined up horizontally and vertically and further improving a method for charge binning identification and method for generating the $\phi V$ signal and $\phi H$ signal, the present embodiment can sum electric charge on the solid-state imaging element and improve image sensitivity.

Figure 12:
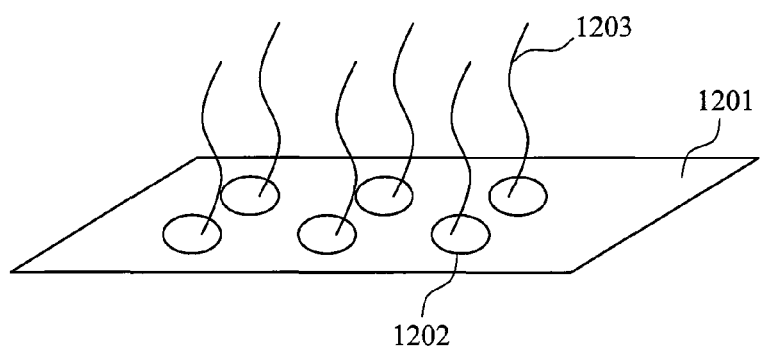
FIG. 12 is a diagram showing an example of a reaction device used on an analyzing apparatus according to a third embodiment.

FIG. 12 shows an example of a reaction device expected to be used in the present embodiment, where the reaction device has a structure in which reaction spots are lined up. Reaction spots 1202 are arranged on a substrate 1201 made of silicon or another semiconductor with or without surface treatment. The reaction spots 1202 are created by mounting metal structures or formed by etching or sputtering and holds probes 1203. If shape and material are selected appropriately, the reaction spots 1202 can also generate localized plasmon resonance to enhance fluorescence emission. The most important point is that the reaction spots 1202 are lined up.

Figure 13:
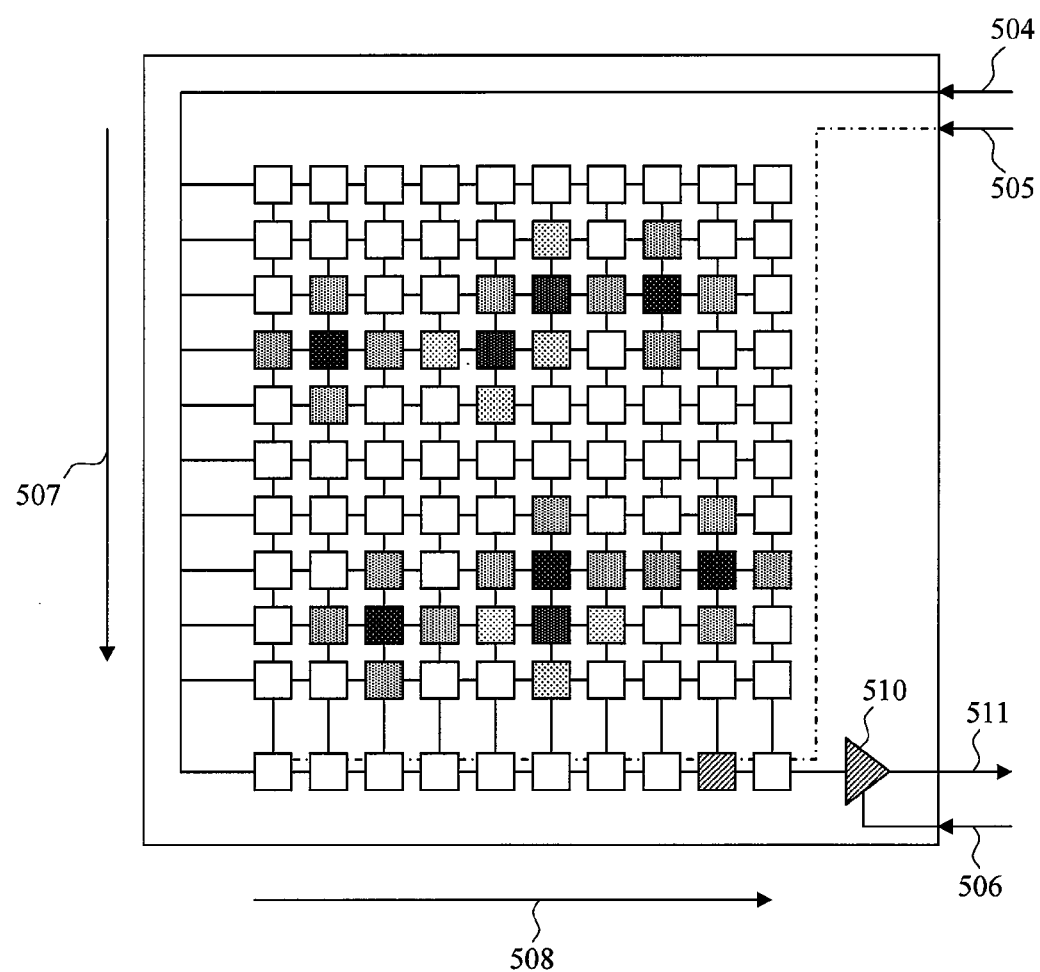
FIG. 13 is a diagram illustrating a solid-state imaging element drive method according to the third embodiment.

FIG. 13 shows exemplary results of preliminary shooting (see Step 902) done with a reaction device such as shown in FIG. 12 by a solidstate image pickup device. For the simplicity of explanation, it is assumed in FIG. 13 that the solid-state imaging element is 10 pixels square. In FIG. 13, state of charge accumulation is represented by density of shading. As shown in FIG. 13, there is not necessarily a one-to-one correspondence between reaction spot locations and pixels. Normally, due to optical distortion or misalignment between the camera and device, it is difficult to bring the reaction spots on the reaction device into one-to-one correspondence with the pixels of the solid-state imaging element. Consequently, each bright spot often spreads over plural pixels as shown in FIG. 13. In such a case, simple charge/voltage conversion and A/D conversion of a single pixel do not provide sufficient bright-spot information about the bright spot and it is considered that a value summed over neighboring pixels will provide more accurate bright-spot luminance information.

Procedures for image shooting under such conditions will be described with reference to FIG. 14.

Figure 14:
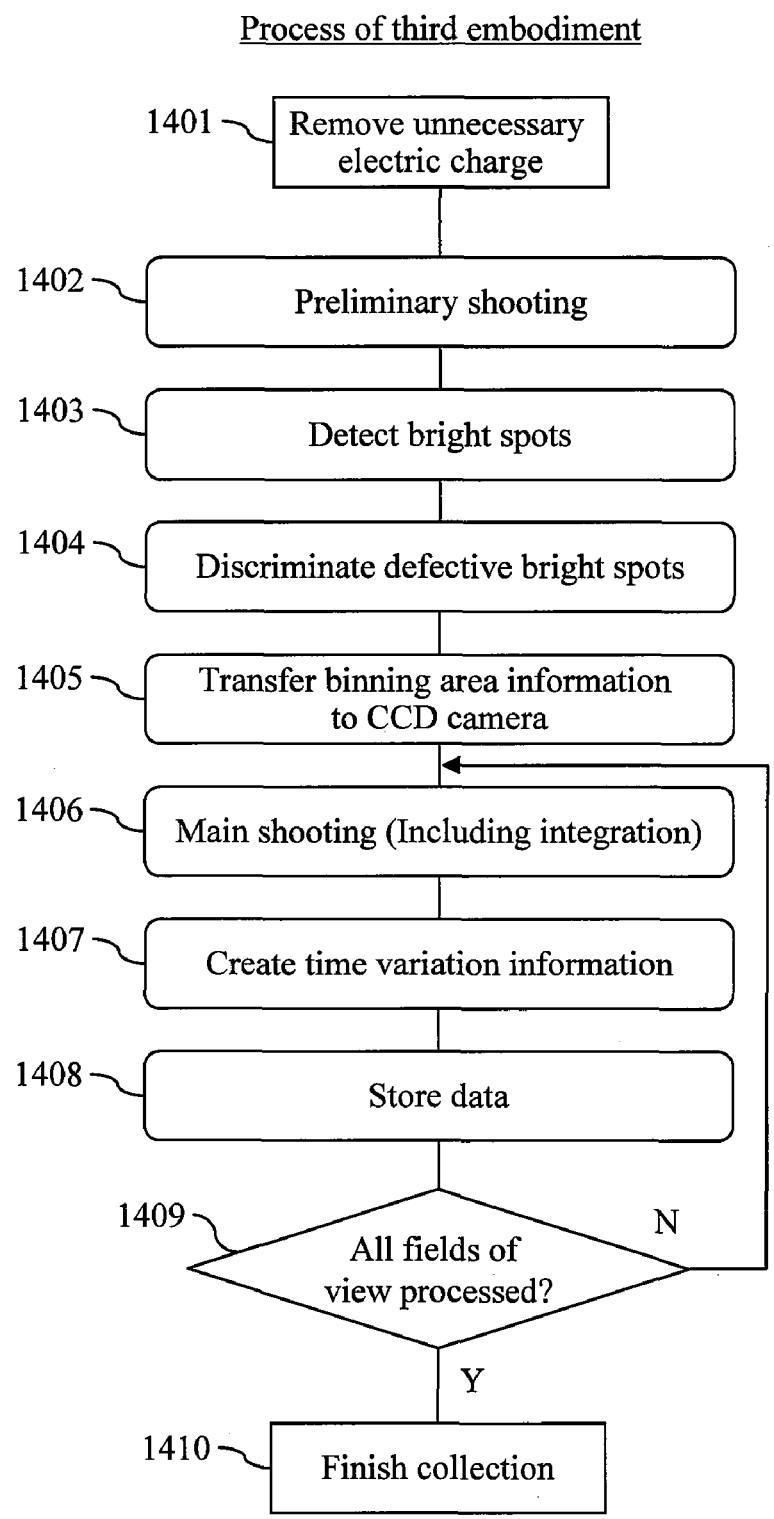
FIG. 14 is a flowchart of a data collection method performed on an analyzing apparatus according to the third embodiment.

In the image shooting procedures according to the present embodiment shown in FIG. 14, Steps 1401 to 1404 correspond to Steps 901 to 904 according to the first embodiment. On the other hand, information which represents binning areas 1505 such as shown in FIG. 15 is transferred in Step 1405 instead of the binning position information transferred in Step 905.

Next, in Step 1406, the camera control MPU 201 does main shooting. When binning areas are defined instead of binning positions, main shooting involves collecting electric charge only from pixels in binning areas detected by preliminary shooting in advance, integrating the electric charge of bright spots in the bright-spot areas, carrying out charge/voltage conversion and A/D conversion of the integrated electric charge, and transferring bright-spot information about only necessary bright spots as digital values to the computer in sequence. Concrete procedures are shown below.

Figure 15:
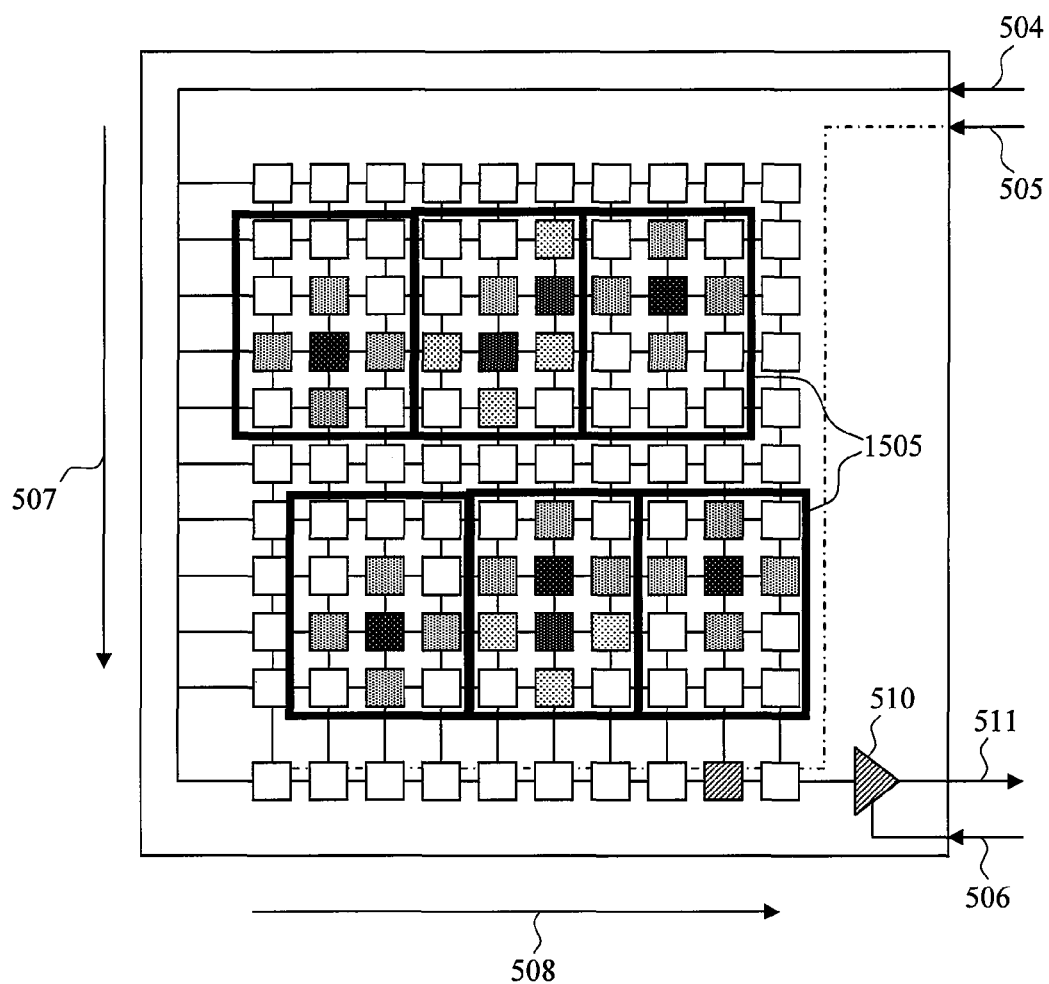
FIG. 15 is a diagram illustrating the solid-state imaging element drive method according to the third embodiment.
Figure 16:
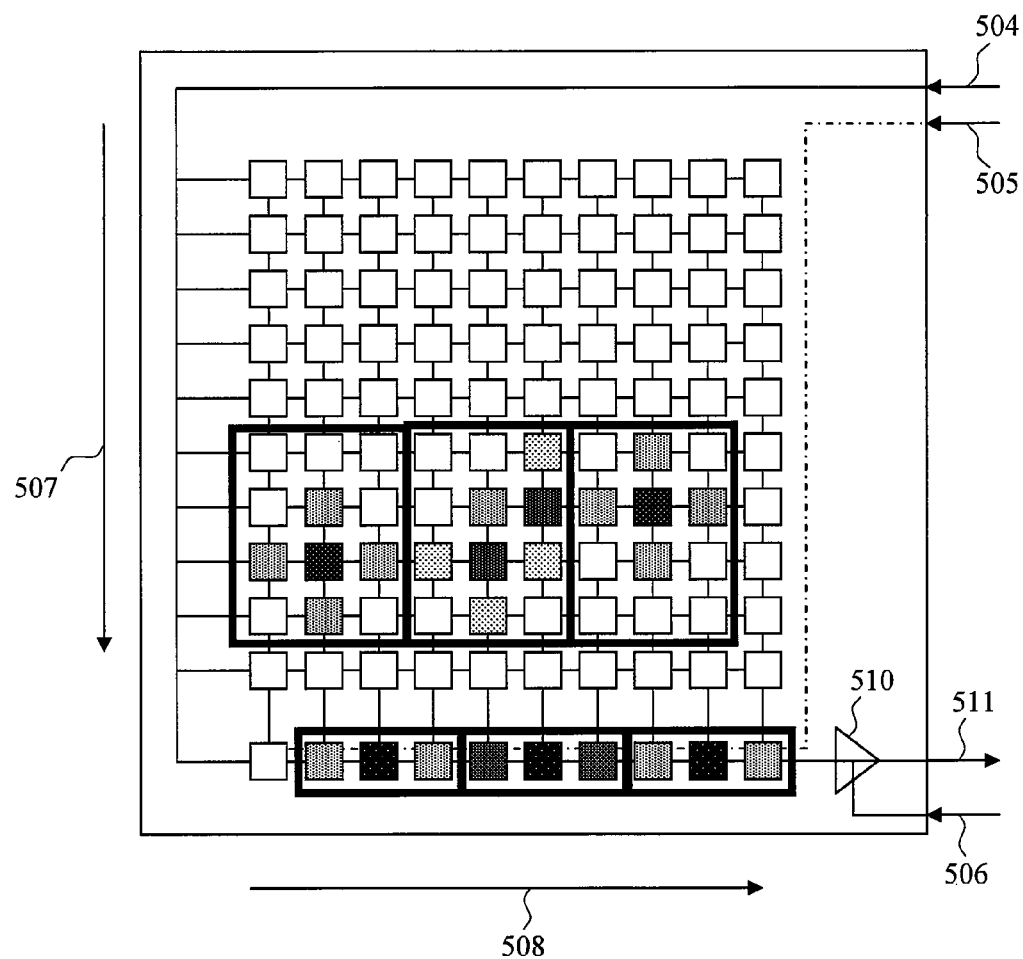
FIG. 16 is a diagram illustrating the solid-state imaging element drive method according to the third embodiment.
Figure 17:
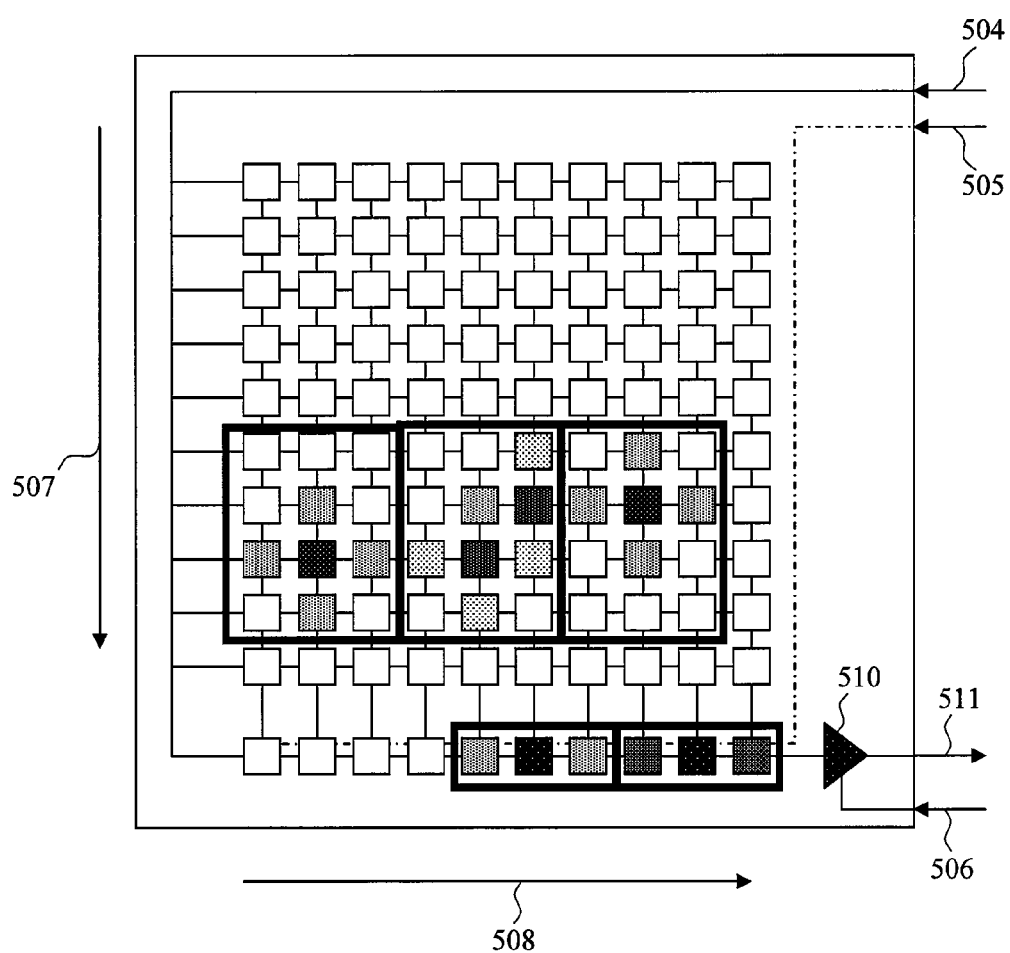
FIG. 17 is a diagram illustrating the solid-state imaging element drive method according to the third embodiment.

That areas of the combined light-receiving and vertical transfer element which corresponds to the three bright spots on the near side of the reaction device in FIG. 12, i.e., the lower three of the binning areas 1505 in FIG. 15, are arrays of four rows by three columns. When four pulses of the φV signal are given, the amount of electric charge summed over the four pixels in the vertical direction shown in FIG. 16 is stored in the horizontal transfer elements. Next, three pulses of the φH signal are given to transfer the electric charge from three columns to the charge/voltage converter 510. Consequently, the electric charge summed over the given bright-spot areas is stored in the charge/voltage converter 510 (FIG. 17). In this state, charge/voltage conversion and A/D conversion are carried out, producing a single digital value corresponding to one reaction spot.

Similarly, to obtain a summed luminance value of a next reaction spot, three pulses of the φH signal are given and charge/voltage conversion and A/D conversion are carried out.

Figure 18:
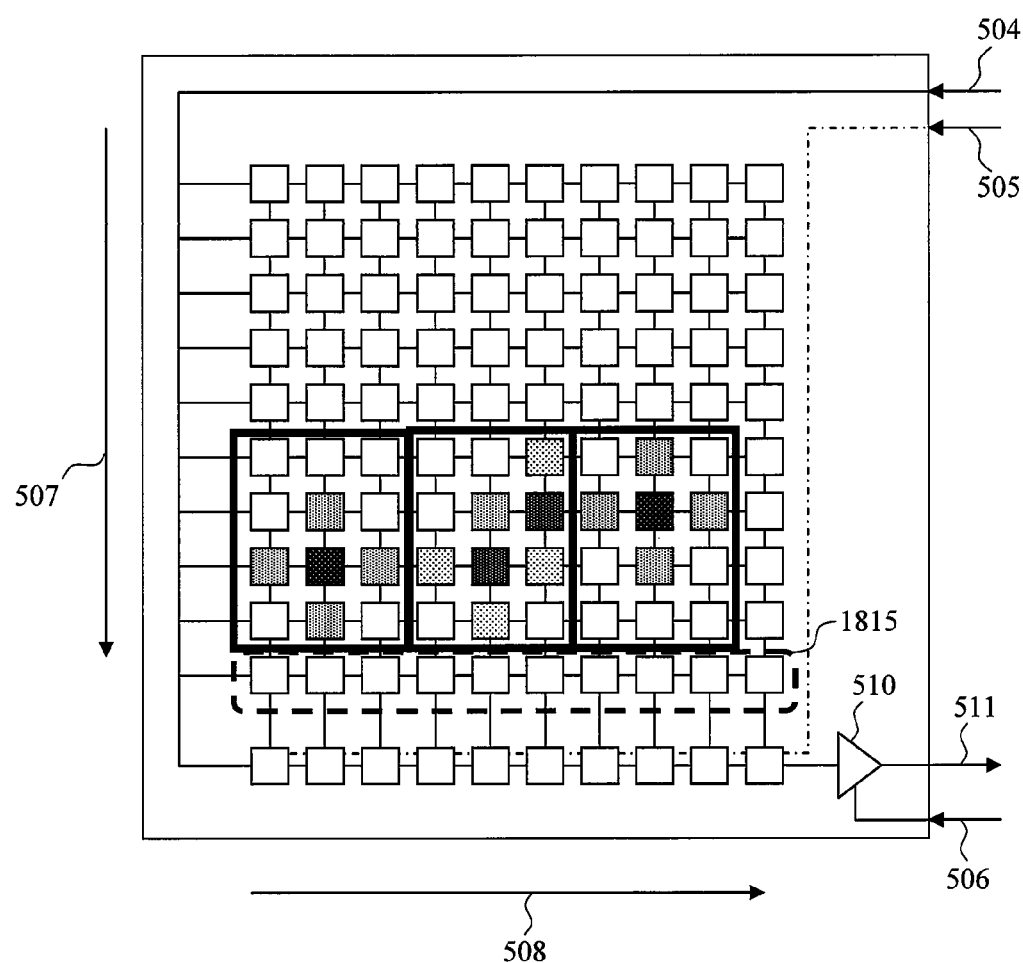
FIG. 18 is a diagram illustrating the solid-state imaging element drive method according to the third embodiment.

FIG. 18 shows a state which results upon completion of the conversion into luminance values of the three bright spots on the near side of the reaction device in the example of FIG. 12. Next, it is necessary to collect electric charge accumulated in pixels corresponding to the bright spots on the far side of the reaction device. Before that, electric charge in an unnecessary pixel row 1815 needs to be removed. For that, it is necessary only to give one pulse of the φV signal and ten pulses of the φH signal corresponding to the number of horizontal pixels.

Figure 19:
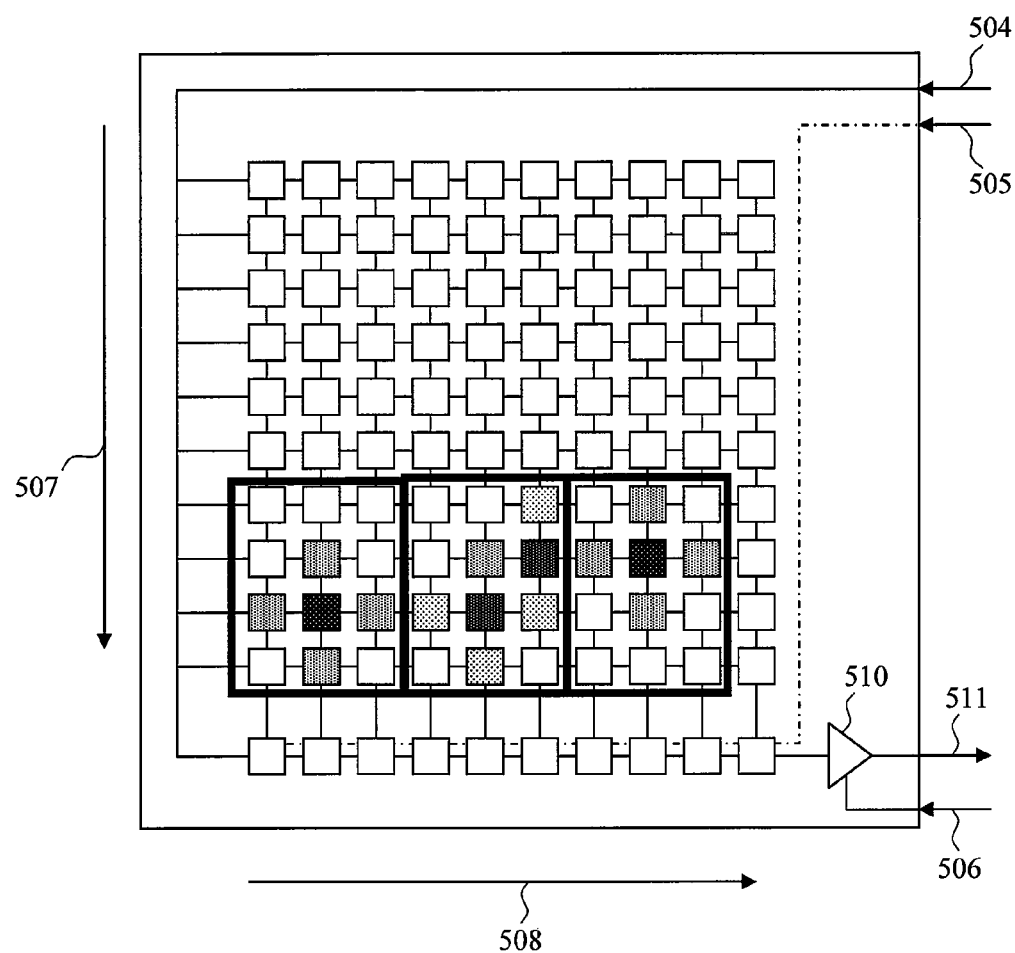
FIG. 19 is a diagram illustrating the solid-state imaging element drive method according to the third embodiment.

A state which results when the unnecessary electric charge is removed is shown in FIG. 19.

Subsequently, to collect luminance values, digital values corresponding on a one-to-one basis to reaction spots are collected, as described above, using pulses of the φV signal and φH signal corresponding to the number of pixels over which electric charge is summed.

Returning to FIG. 14, Step 1407 and subsequent steps are the same as the procedures shown in FIG. 9.

A pixel range defined by the binning area according to the present embodiment does not need to be fixed and may vary with the bright spot. Also, binning-area intervals which correspond to bright-spot intervals do not need to be equal, and may be set to be unequal.

As described above, by averaging or summing a few pixels around a bright spot, it is possible to obtain a summed digital value of luminance information about the reaction spot, greatly reducing the amount of image processing on the analyzing computer compared to full-frame collection as well as greatly reducing the amount of data transferred from the CCD camera unit to the analyzing computer. This makes it possible to implement a nucleic acid analyzing apparatus which can improve image processing speed while achieving the intended purpose—to obtain summed luminance values.

Incidentally, in the field of camera systems, there is a conventional technique which increases apparent sensitivity by doing binning while summing $2^n$ lines of electric charge in the row or column direction on a solid-state imaging element, for the purpose of improving processing speed. However, to do binning while performing summation, it is necessary to specify the number of summed lines in terms of $2^n$. With an apparatus to which the present embodiment is applicable, i.e., a nucleic acid analyzing apparatus for single molecule fluorescence observation, thousands to tens of thousands of reaction spots need to be lined up in about $2^n$ lines 6 µm in width which corresponds to pixel size of a CCD. With currently available microfabrication techniques, optical-system design techniques, and the like, it is not practical to shoot fluorescence with such high accuracy.

Fourth Embodiment

The first to third embodiments described above use a solid-state imaging element in which light-receiving elements are arranged two-dimensionally. Besides, fluorescence may be scanned using a one-dimensional CCD in which light-receiving elements are arranged in a line, as described in Patent Document 1. In that case, the φV signal according to the present invention corresponds to a moving step for a unit which includes the light-receiving elements and the φH signal corresponds to pixel charge transfer from the one-dimensional CCD.

A fluorescence scanning apparatus with a one-dimensional CCD operates in a manner similar to the one described in the first embodiment, and procedures will be described below briefly.

Instead of the preliminary shooting according to the above embodiments, pre-scanning is performed to shoot an entire image of a reaction device. Next, from an image obtained by pre-scanning, targeted bright-spot locations are detected and defective bright spots are discriminated. Then, only the detected bright-spot locations are finally scanned and targeted bright-spot information is collected.

Thus, when the method according to the present embodiment is applied to a scanning system, there is no need to turn on a light source except at targeted scanning positions. This allows a scanning system which uses long-life parts such as a semiconductor laser element to operate for a longer time although an additional circuit or software is needed for turn-on/turn-off control. Also, since only necessary bright spots are scanned and subjected to charge/voltage conversion and A/D conversion, it is possible to greatly reduce the amount of image processing on the analyzing computer compared to full-range scanning as well as greatly reduce the amount of data transferred from the one-dimensional CCD camera unit to the analyzing computer. This makes it possible to reduce scanning time and improve image processing speed.

Although the above embodiments have been described based on a real-time method which produces a sequencing reaction in real time, the present invention is also applicable to a consecutive reaction system which controls quenching and elongation reaction of fluorescent dyes. Also, although the above embodiments have been described based on a system in which nucleic acid probes are fastened to a reaction device, the present invention is also applicable to a system in which nucleic acid synthetase is fastened to a reaction device. Also although the above embodiments have been described based on single molecule sequencing method which uses single molecule nucleic acid probes, the present invention is also applicable to a sequencing method which uses a small number—two to a few tens—of nucleic acid probes (clusters).

The specifications and papers cited herein are part of the present specification and can be referred to for details of DNA sequencing.

What is claimed is:

1. A nucleic acid analyzing apparatus equipped with an imaging element for use to image a reaction device, comprising:

a preliminary shooting section which shoots the reaction device using the imaging element;

a bright-spot detection section which transmits data generated by A/D conversion of an entire area of an image obtained by preliminary shooting to an analyzing computer via a communications control interface in a camera unit, detecting only bright-spot coordinates of the reaction device in the data, and stores the bright-spot coordinates as first binning positions;

a defective bright-spot discriminating section which discriminates and deletes any defective bright spot from the first binning positions, calculates only predetermined bright-spot information, and stores the calculated bright-spot information as second binning positions, in the analyzing computer;

a binning-position information transfer section which transmits information about the second binning positions from the analyzing computer back to a camera control MPU via an apparatus control computer and the communications control interface in the camera unit; and a main shooting section which collects images by varying a drive signal to selectively collect only imaging-element information included in the second binning positions.

2. The nucleic acid analyzing apparatus according to claim 1, wherein the imaging element is a solid-state imaging element.

3. The nucleic acid analyzing apparatus according to claim 1, wherein the imaging element is a one-dimensional photosensor and the reaction device is scanned using the preliminary shooting section and the main shooting section to observe fluorescent bright spots on the reaction device.

4. A nucleic acid analyzing apparatus equipped with an imaging element for use to image a reaction device, comprising:

a preliminary shooting section which shoots the reaction device using the imaging element;

a bright-spot detection section which transmits data generated by A/D conversion of an entire area of an image obtained by preliminary shooting to an analyzing computer via a communications control interface in a camera unit, detects only bright-spot coordinates of the reaction device in the data, and stores the bright-spot coordinates as first binning areas at unequal intervals;

a defective bright-spot discriminating section which discriminates and deletes any defective bright-spot from the first binning areas, calculates only predetermined bright-spot information, and stores the calculated bright-spot information as second binning areas, in the analyzing computer;

a binning-area information transfer section which transmits information about the second binning areas from the analyzing computer back to a camera control MPU via an apparatus control computer and the communications control interface in the camera unit; and a main shooting section which selectively sums a plurality of pieces of imaging-element information collected near bright spots calculated as the second binning areas, converts the summed imaging-element information into digital values; and collects images by varying a drive signal to selectively collect only imaging-element information included in the second binning areas.

5. The nucleic acid analyzing apparatus according to claim 4, wherein the first binning areas are preset in a storage device.

6. A nucleic acid analyzing apparatus equipped with an imaging element for use to image a reaction device, comprising:

a main shooting section which shoots the reaction device using the imaging element;

a bright-spot detection section which transmits data generated by A/D conversion of an entire area of an image obtained by main shooting to an analyzing computer via a communications control interface in a camera unit, detecting only bright-spot coordinates of the reaction device in the data;

a defective bright-spot discriminating section which discriminates and deletes any defective bright-spot from the detected bright-spot coordinates and calculates only predetermined bright-spot information, in the analyzing computer;

a multi-area bright-spot information integrating section which integrates bright-spot information over a plurality of areas in the bright-spot coordinates calculated by the bright-spot detection section and the defective bright-spot discriminating section, in the analyzing computer; and a intensity trace data collecting section which collects changes in the integrated bright-spot information with time, analyzes a change pattern of a bright spot, and thereby determines whether the bright spot is a desired one, in the analyzing computer.

* * * * *